United States Patent [19]

Ehrl

[11] Patent Number: 4,613,308

[45] Date of Patent: Sep. 23, 1986

[54] JAW IMPLANT HAVING AN APERTURE TO RECEIVE A REPLACEMENT-TOOTH HOLDER

[75] Inventor: Peter A. Ehrl, Freudenstadt, Fed. Rep. of Germany

[73] Assignee: Feldmühle Aktiengesellschaft, Düsseldorf, Fed. Rep. of Germany

[21] Appl. No.: 738,695

[22] Filed: May 28, 1985

[51] Int. Cl.[4] .............................................. A61C 8/00
[52] U.S. Cl. ................................................... 433/173
[58] Field of Search ................................ 433/175, 173

[56] References Cited

U.S. PATENT DOCUMENTS 2,210,424  8/1940  Morrison .............................. 433/175
3,343,263  9/1967  Henlotter ............................. 433/175
4,215,986  8/1980  Reiss ..................................... 433/173
4,304,553 12/1981  Heimke et al. ...................... 433/173

Primary Examiner—Robert Peshock
Attorney, Agent, or Firm—Felfe & Lynch

[57] ABSTRACT

A jaw implant shaped and proportioned to provide firm seating and sufficiently great resistance to tractive forces. The implant has a bore for receiving a tooth holder and has at its apical end a spherical segment. The implant has truncoconical portions and an approximately cylindrical portion provided for embedding in the cortical bone tissue. The truncoconical portions and the approximately cylindrical portion have approximately elliptical cross sections.

7 Claims, 5 Drawing Figures

JAW IMPLANT HAVING AN APERTURE TO RECEIVE A REPLACEMENT-TOOTH HOLDER

The present invention relates to a jaw implant having an aperture for receiving a replacement-tooth holder, and having on its apical end the shape of a spherical segment exceeding the size of a hemisphere, which merges in the direction toward the aperture with a divergent portion.

Jaw implants are disclosed in German Pat. No. 583,421 and in German publications OS Nos. 25 49 114 and 27 43 035. In German Pat. No. 583,421, an implant similar in its external shape to the natural tooth root is proposed, while the later proposals provide for the formation of certain constrictions, annular surfaces perpendicular to the central axis of the implant, flats, or areas of circular cross section diverging in the direction toward the coronal end, by which the ingrowth of the bone tissue is to be promoted and a secure seating of the implant is to be achieved. The common disadvantage of these known jaw implants is that they have a relatively great cross-sectional area in the part which is provided for embedding in the epithelium and bone eruption point. In accordance with DE-OS No. 27 43 035, in an implant post diverging in the coronal direction, provision is made for the area at which the post emerges from the jaw bone to be limited to the smallest possible size, and for this purpose an inversely conical peripheral surface adjoins the divergent portion, but even in this known implant, the section to be inserted into the epithelium and bone eruption point still has a very great cross-sectional area, creating the danger that cratering will develop in this area, because here the bone tissue is not apposed horizontally.

An object of the present invention is to provide an implant which, on account of its shape, is to have an improved ingrowth, and especially to avoid the undesirable cratering better than formerly, so that, after the healing-in phase, the implant will have a firm seat and offer sufficiently great resistance to any tractive forces that might occur.

The term "approximately elliptical" used in the specification and claims also covers an oval cross-sectional shape of the jaw implant.

The configuration of the portion of elliptical cross section diverging in the direction toward the bore provides the implant with a very extensive security against torsion. In this manner, right from the beginning, a certain fixation of the implant is achieved and the healing-in process is better promoted than in the former implants which in this area were of a truncoconical configuration with a circular cross section. Since the jaw implant of the invention is of an approximately cylindrically shaped configuration with a wall parallel to the longitudinal axis in its portion designed for embedding in the cortical bone, this area has a very small cross-sectional area, so that here a horizontal apposition of the bone tissue can take place, so that the undesirable cratering is largely absent. After the healing-in process has been completed, the convergent shape of the portion following upon the apical end comprising the spherical segment provides a sufficiently great resistance to tractional forces that may occur. An additional advantage lies, in the jaw implant of the invention, as a result of its elliptical cross section, in the fact that the implant can be used even at those points in the jaw crest at which a certain jaw atrophy has occurred, i.e., the jaw crest has thinned at this point. The implant is inserted, depending on the width of the alveolar crest, such that the greater cross-sectional radius runs in the mesiodistal or vestibular direction. The known implants with their relatively large cross sections in the areas which are to be inserted into the cortical bone have been used in such cases with extreme rarity.

Preferably, the implant in accordance with the invention is used as a so-called "late implant", i.e., after the extraction, the regeneration of the bone tissue is first awaited, and then a hole is drilled in it whose diameter corresponds approximately to the maximum diameter of the section that diverges in the direction toward the bore and comes after the spherical segment. However, this method of implantation is not obligatory, and the implant can in suitable cases be used as an immediate implant.

In accordance with the invention, a jaw implant comprises an apical end comprising a spherical segment exceeding the size of a hemisphere. The implant includes a first truncoconical portion following upon the apical end, the cross-sectional area of the first truncoconical portion increasing in the coronal direction. The implant also includes a second truncoconical portion following without transition upon the first portion, the cross-sectional area of the second truncoconical portion decreasing in the coronal direction. The implant also includes a third approximately cylindrically shaped portion adjoining the second portion and provided for embedding in the cortical bone tissue. The implant also includes a fourth truncoconical portion following the third portion and having a cross-sectional area increasing in the coronal direction. The height of the first portion is greater than the height of the second portion. At least the fourth portion has an opening provided for the accomodation of a tooth holder, and the first, second, third and fourth portions have approximatley elliptical cross sections.

For a better understanding of the invention, together with other and further objects thereof, reference is made to the following description, taken in connection with the accompanying drawings, and its scope will be pointed out in the appended claims.

Referring now to the drawings.

Figure 1:
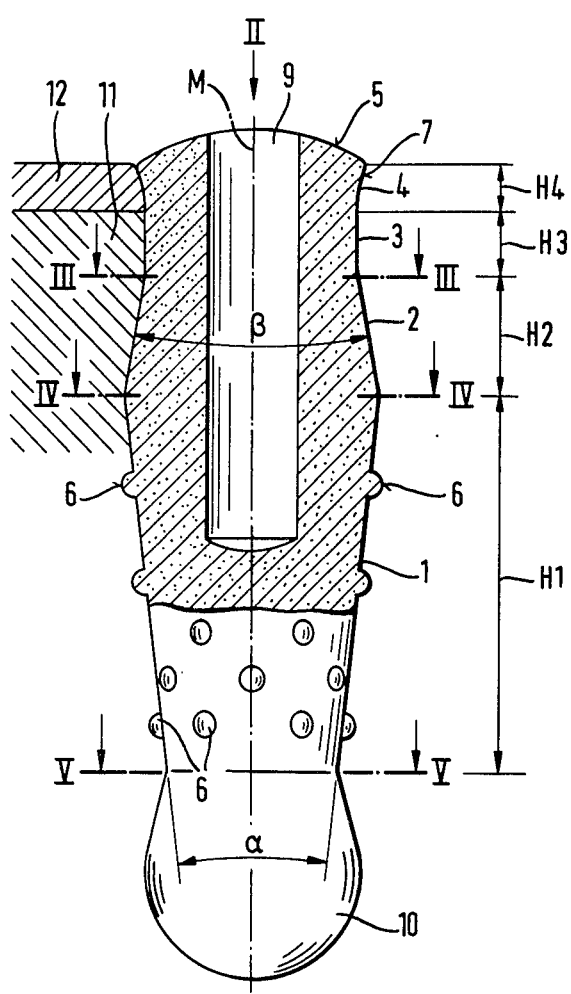
FIG. 1 is a partially sectioned, diagrammatic side view of the jaw implant of the invention, in which the cortical bone and gingival tissue are represented on one side in simplified form.

FIG. 1 shows a jaw implant 8 in accordance with the invention, preferably made from high-purity aluminum oxide, which has at its apical end a spherical segment 10. The spherical segment 10 merges with the portion 1 which diverges toward the bore 9 preferably with a flare angle $\alpha = 13°$ and preferably with a height H1 of 9 mm. In portion 1 with the height H1 of 9 mm, preferably hemispherical knobs 6 are formed. Portion 1 has its greatest cross-sectional area in the region of the line IV—IV, before it merges with the convergent portion 2 preferably with a height H2 of 3 mm. Adjoining portion 2 is the approximately cylindrical portion 3 which is provided for apposition of cortical bone 11. Portion 3 preferably has a height H3 of 1.5 mm and merges evenly with the divergent portion 4. To achieve a flush termination, the top 5 of the divergent portion 4 preferably is rounded off with a radius of R=5 cm. The implant 8 preferably is inserted so that the above-described rounding projects above the gingivae 12, so that, after the tooth holder (not shown) is installed, the possibility exists for modeling the replacement tooth on the replacement tooth holder such that the gingivae will be virtually flush with the rounded top 5. The external contours 7 of portion 4 preferably are convex, i.e., they curve inwardly toward the longitudinal axis M of the implant 8. The aperture angle $\beta$ of portion 2 preferably amounts to 19 degrees.

Figure 3:
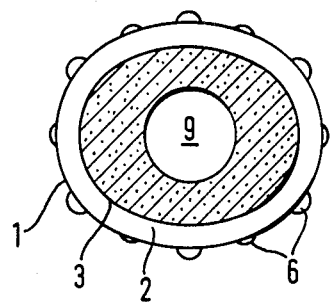
FIG. 3 is a cross-sectional view of the implant, taken along line III—III of FIG. 1.
Figure 4:
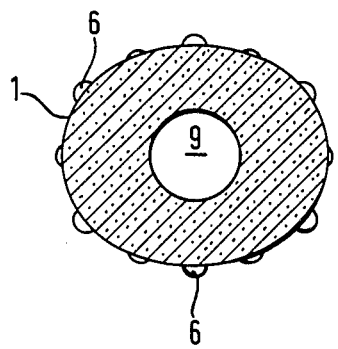
FIG. 4 is a cross-sectional view of the implant, taken along line IV—IV of FIG. 1.
Figure 2:
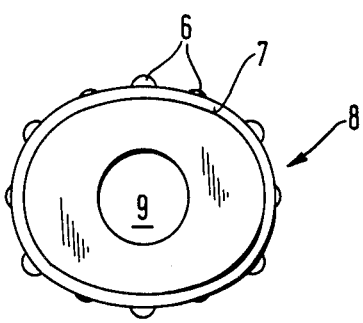
FIG. 2 is a top view of the jaw implant of FIG. 1, taken in the direction of arrow II.

FIG. 2 is a plan view of the aperture 9 for accommodating the tooth holder (not shown) which is fastened by its shank in the bore 9. FIGS. 2, 3 and 4 show the elliptical top configuration of portion 4 and the elliptical cross-sectional configurations of portions 2 and 1. The cross-sectional configuration of portion 3 is the same as that shown by FIG. 3 for portion 2. As can be seen in FIG. 3, the knobs 6 can be provided up to the bottom of the portion 3. Their hemispherical profile configuration reduces the occurrence of peak tensions in the bone tissue surrounding them.

Figure 5:
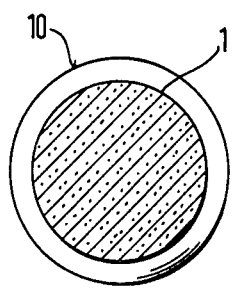
FIG. 5 is a cross-sectional view of the implant, taken along line V—V of FIG. 1.

As can be seen in FIG. 4, the spherical segment merges in the area of the line V—V with the divergent portion 1 which has an elliptical cross section. As represented in FIG. 5, the diameter of the spherical segment 10 is smaller than the maximum diameter in the area of the line IV—IV of portion 1 and the corresponding diameter of the convergent portion 2.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A jaw implant comprising:
   an apical end comprising a spherical segment exceeding the size of a hemisphere;
   a first truncoconical portion following upon said apical end, the cross-sectional area of said first truncoconical portion increasing in the coronal direction;
   a second truncoconical portion following without transition upon said first portion and having a height of of 3 to 6 mm, the cross-sectional area of said second truncoconical portion decreasing in the coronal direction;
   a third approximately cylindrically shaped portion adjoining said second portion and having a height of 1 to 3 mm and provided for embedding in the cortical bone tissue; and
   a fourth truncoconical portion following said third portion and having a height of 1 to 2 mm and having a cross-sectional area increasing in the coronal direction;
   the height of said first portion being greater than the height of said second portion;
   at least said fourth portion having an opening provided for the accommodation of a tooth holder;
   said first, second, third and fourth portions having approximately elliptical cross sections.

2. A jaw implant in accordance with claim 1, in which said first frustococonical portion comprises knobs of hemispherical profile formed thereon.

3. A jaw implant in accordance with claim 1, in which said first frustoconical portion has a flare angle alpha of 10 to 15 degrees.

4. A jaw implant in accordance with claim 1, in which said second frustoconical portion has a flare angle beta of 16 to 22 degrees.

5. A jaw implant in accordance with claim 1, in which the longitudinal and transverse radii of the minimum sectional area of said second portion are 10–27% smaller than the radii of the maximum sectional area of said first portion.

6. A jaw implant in accordance with claim 1, in which the longitudinal and transverse radii in the approximately elliptical maximum and minimum sectional areas of said first truncoconical portion, in the minimum sectional area of said second truncoconical portion, and in the approximately elliptical maximum sectional area of said third truncoconical portion differ from one another by not more than 1.3 times.

7. A jaw implant in accordance with claim 1, which comprises high-purity aluminum oxide.

* * * * *